_(12)_ United States Patent
Tseng et al.

(10) Patent No.: US 8,778,661 B2
(45) Date of Patent: Jul. 15, 2014

(54) BIOLOGICAL COMPOSITE AND METHOD FOR REDUCING $H_2S$

(75) Inventors: Ching-Ping Tseng, Hsinchu (TW); Yu-Pei Chen, New Taipei (TW)

(73) Assignee: National Chiao Tung University, Hsinchu (TW)

( * ) Notice: Subject to any disclaimer, the term of this patent is extended or adjusted under 35 U.S.C. 154(b) by 39 days.

(21) Appl. No.: 13/418,005

(22) Filed: Mar. 12, 2012

(65) Prior Publication Data

US 2013/0115672 A1    May 9, 2013

(30) Foreign Application Priority Data

Nov. 8, 2011  (TW) .............................. 100140774 A (51) Int. Cl.
| | | |
|---|---|---|
| *B01D 53/52* | (2006.01) | |
| *B01D 53/84* | (2006.01) | |
| *C12N 11/14* | (2006.01) | |
| *C12N 11/00* | (2006.01) | |
| *C12N 11/02* | (2006.01) | |
| *C10L 3/10* | (2006.01) | |
| *C12N 1/20* | (2006.01) | |

(52) U.S. Cl.
USPC .......... 435/266; 435/174; 435/176; 435/262.5

(58) Field of Classification Search
CPC ........ B01D 53/52; B01D 53/84; C12N 11/14; C12N 11/00; C12N 11/02; C12N 1/20; C10L 3/103
See application file for complete search history.

(56) References Cited

PUBLICATIONS

Rattanapan ("Removal of H2S in down-flow GAC biofiltration using sulfide oxidizing bacteria from concentrated latex wastewater" Bioresource Technology, 2009, 100, 125-130).*
Skirnisdottir ("Isolation and characterization of a mixotrophic sulfur-oxidizing Thermus scotoductus" Extremophiles 2001, 5, 45-51).*

* cited by examiner

*Primary Examiner* — Blaine Lankford
*Assistant Examiner* — Charles Zoltan Constantine
(74) *Attorney, Agent, or Firm* — Muncy, Geissler, Olds & Lowe, P.C.

(57) ABSTRACT

A biological composite and method for reducing $H_2S$ are disclosed. The biological composite for reducing $H_2S$ includes a carrier and *Thermus* sp. immobilized on the carrier. Therefore, if a sample containing $H_2S$ has contact with *Thermus* sp. or the carrier with *Thermus* sp. immobilized thereon, the amount of $H_2S$ can be reduced.

5 Claims, 8 Drawing Sheets

BIOLOGICAL COMPOSITE AND METHOD FOR REDUCING $H_2S$

CROSS REFERENCE TO RELATED APPLICATION

This application claims the benefits of the Taiwan Patent Application Serial Number 100140774, filed on Nov. 8, 2011, the subject matter of which is incorporated herein by reference.

BACKGROUND OF THE INVENTION

1. Field of the Invention

The present invention relates to a biological composite and a method for reducing $H_2S$.

2. Description of Related Art

Biogas from a wastewater treatment plant is classified as a cheap and environmentally friendly renewable energy, and can be applied as a source of alternative vehicle fuel or in generation of heat, electricity, and chemical compounds. Generally, such biogas contains 65% methane, 30% $CO_2$, 4% $N_2$, 0.2% $H_2S$, and other minor gases. Notably, $H_2S$ is found in production of biogas and natural gas, or in the process of papermaking or oil-refining. When the accumulation of $H_2S$ reaches a concentration up to 1000 ppm or more, it causes serious erosion to machines such as dynamos, and can be lethal to humans. Therefore, there is a need to reduce $H_2S$ as much as possible in relevant processes.

Currently, methods for removing gaseous $H_2S$ are mainly physical methods; incineration, Claus process, chemical washing; as well as biological methods. Except for biological methods, the others require high costs due to replacement of consumable materials or setting up of equipment. However, even in biological methods, there are still limitations in the treatment of $H_2S$ up to 1000 ppm or more, depending on oxidative activity of different microbes to $H_2S$. Besides, when $H_2S$ is oxidized into $H_2SO_4$ by microbes, $H_2SO_4$ is accumulated and makes the environmental pH value decrease. Accordingly, the growth and activity of the microbes are undesirably influenced, thereby resulting in decreased removal of $H_2S$.

Therefore, there is a need to find a microbe with extremely strong capacity for $H_2S$ oxidation. Even if the environmental pH value is decreased, the microbe should be able to retain good oxidative activity to $H_2S$ and thus it is advantageous to promote the environmental control development efforts within the papermaking and oil-refining industries as well as in the production of biogas and natural gas.

SUMMARY OF THE INVENTION

The object of the present invention is to provide a biological composite and a method for reducing $H_2S$. They can be applied to reduce the $H_2S$ amount in related industries such as environmental and petrochemical industries, food engineering, and livestock farming so that serious erosion to machines and lethal injury to humans can be prevented.

To achieve the object, one aspect of the present invention provides a biological composite for reducing $H_2S$, comprising: a carrier; and *Thermus* sp. bacterium immobilized on the carrier.

Another aspect of the present invention provides a biological method for reducing $H_2S$, comprising the following step: making *Thermus* sp. bacterium in contact with a sample containing $H_2S$.

In the biological method for reducing $H_2S$ mentioned in the present invention, the *Thermus* sp. bacterium can be immobilized on a carrier. Thus, if the carrier has contact with the $H_2S$-containing sample, the amount of $H_2S$ can be reduced.

In the biological method and composite for reducing $H_2S$ mentioned in the present invention, the carrier can be activated carbon, peat soil, compost, bark, vermiculite, oyster shell, zeolite, porphyritic andesite, iron hydroxide, active alumina, pearlite, snakewood, artificially synthesized chemical materials, or a combination thereof. Among them, the artificially synthesized chemical materials can be high molecular weight polymers such as polyethylene foam and Styrofoam. The *Thermus* sp. bacterium can form a biofilm encompassing the carrier, or form a biofilm along the outside and the inner pores of the carrier.

Still another aspect of the present invention provides an acidophilic sulfide-oxidizing bacterium, which is *Thermus* sp. bacterium and of which 16S rDNA sequence comprises SEQ ID NO. 3.

The bacterium was deposited on Oct. 19, 2011 and as BCRC 910527 in Bioresource Collection and Research Center in Hsinchu, Taiwan.

In addition to the bacterium mentioned above, the *Thermus* sp. bacterium can also be *Thermus scotoductus*.

In conclusion, during petrochemical oil-refining process, biogas and natural gas production, and papermaking process, $H_2S$ accumulation can reach an amount more than 1000 ppm and thus cause erosion to machines or dynamos and be lethal to humans. However, the biological method and composite of the present invention can be applied to reducing $H_2S$ in related industries as mentioned above. In other words, through the method and composite of the present invention, the *Thermus* sp. bacterium can transform $H_2S$ gas into $H_2SO_4$ and retain desirable removal efficiency of $H_2S$ in a low pH value, even when the environmental pH value decreases as $H_2SO_4$ accumulates. Accordingly, resource recovery such as purification of biogas and waste gas can be achieved.

Other objects, advantages, and novel features of the invention will become more apparent from the following detailed description when taken in conjunction with the accompanying drawings.

DETAILED DESCRIPTION OF THE PREFERRED EMBODIMENT

The inventors isolated an acidophilic microbe from swine sludge and found that it is tolerant of a low pH value and high $H_2SO_4$ concentration. Thus, it is expected that the microbe can achieve desirable removal efficiency of high $H_2S$ concentration (>1000 ppm). Such acidophilic sulfide-oxidizing bacterium was classified into *Thermus* after identification and is able to transform $H_2S$ into sulfate.

The acidophilic sulfide-oxidizing bacterium is cultured, proliferated, collected, concentrated, and then uniformly mixed with carriers or filters. The carriers or the filter materials are exemplified as peat soil, compost, bark, vermiculite, oyster shell, zeolite, porphyritic andesite, iron hydroxide, active alumina, pearlite, snakewood, Styrofoam, polyethylene foam, and so on. The acidophilic sulfide-oxidizing bacterium is immobilized on the carriers or the filter materials (this step is commonly called as namely "immobilization"), and then their mixture forms biofilter materials having a biofilm. The biofilter materials can be applied to remove $H_2S$. For example, the biofilter materials can be deposited in a suitable container serving as a component of a biogas purification system.

In an example of the present invention, it is found that the average of the removal efficiency of $H_2S$ reaches 95% within 219 days of long-term monitoring. Besides, because $H_2S$ is oxidized into $H_2SO_4$ rather than being catalyzed into S, the biofilter can not be obstructed by S when biogas is purified. Also, the occurrence of gas short-circuiting can be prevented. In addition, as the time of the reaction is prolonged, accumulation of sulfate and decrease in pH value do not make the *Thermus* sp. bacterium of the present invention have lower activity of removing $H_2S$. Therefore, the removal efficiency of $H_2S$ from biogas can be maintained.

Because of the specific embodiments illustrating the practice of the present invention, one skilled in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

The drawings of the embodiments in the present invention are all simplified charts or views, and only reveal elements relative to the present invention. The elements revealed in the drawings are not necessarily aspects of the practice, and quantity and shape thereof are optionally designed. Further, the design aspect of the elements can be more complex.

Example 1

Isolation and Identification of Sulfide-Oxidizing Bacterium

All of the reagents, solutions, containers, and instruments were maintained in aseptic conditions during the following experimental period.

The acidic tolerance bacterium was isolated from swine sludge and cultured in the medium (glucose 5 g, $(NH_4)_2SO_4$ 3 g, $KH_2PO_4$ 0.5 g, $MgSO_4 \cdot 7H_2O$ 0.5 g, KCl 0.1 g, $Ca(NO_3)_2$ 12.5 mg, and $FeSO_4 \cdot 7H_2O$ 0.01 mg in 1 liter) for 7 days and harvested by centrifugation (7500×g for 10 min).

Commercially available granular activated carbon (GAC, Taiwan Activated Carbon Industries Company) obtained from coconut shell with a particle size of 4.5 mm was used as the support material for the immobilization of *Thermus* sp. CP1. The bulk density and the specific surface area of the support material were 0.48 g cm$^{-3}$ and 1250 m$^2$ g$^{-1}$, and the pH value thereof was adjusted to 3.0 by $H_2SO_4$. In the present example, the support material is not limited to granular activated carbon, and it also can be peat soil, compost, bark, vermiculite, oyster shell, zeolite, porphyritic andesite, iron hydroxide, active alumina, pearlite, snakewood, Styrofoam, polyethylene foam, and so forth.

The harvested bacterium was resuspended and evenly mixed with about 2.4 kg of pH-adjusted GAC in a tank. During the immobilization period, the fresh broth was replaced until the bacterial count reached nearly $10^8$-$10^9$ CFU (g GAC)$^{-1}$.

Figure 1:
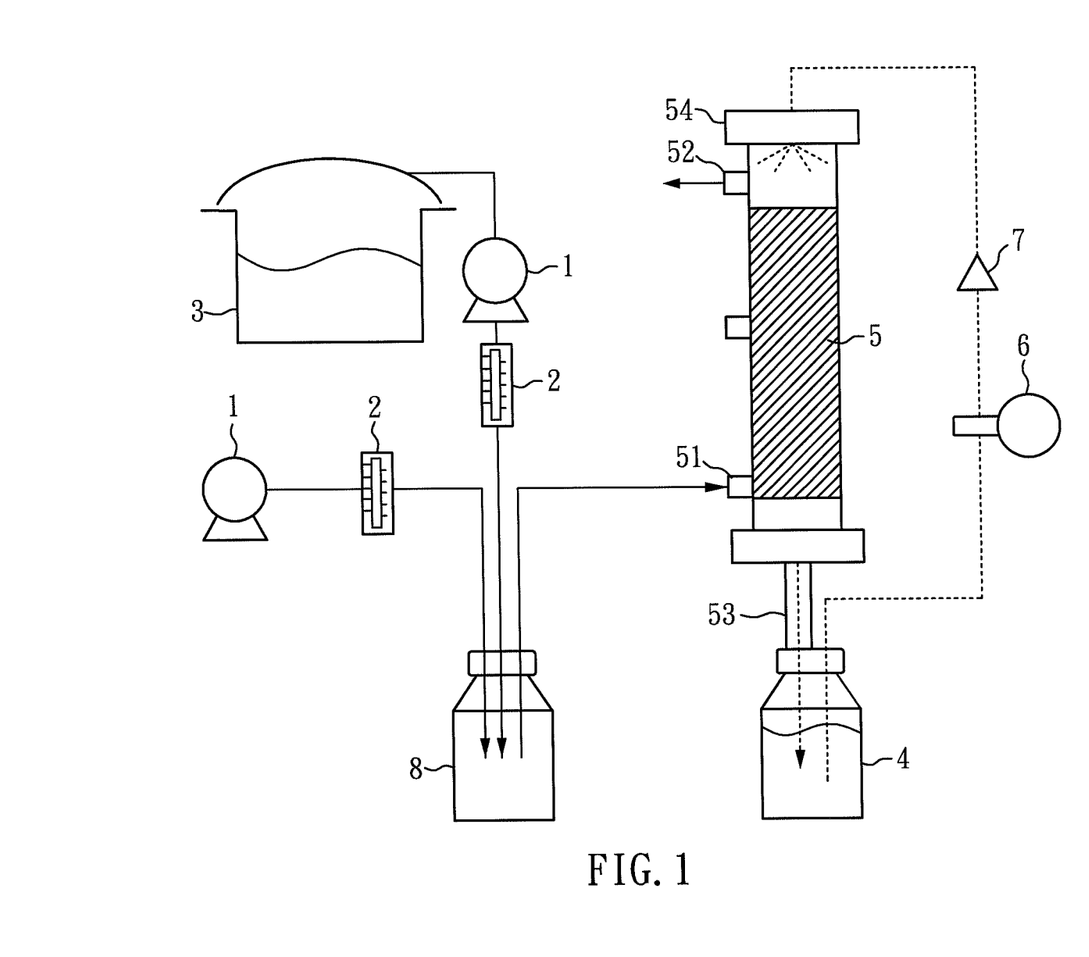
FIG. 1 is a schematic diagram of a field biofilter employed in Examples 1 and 2 of the present invention.

The bacterium-immobilized GAC was packed into a column (diameter 5.5 cm and height 40 cm) of a lab-scaled biofilter (similar to the one shown in FIG. 1). In the column, the packed volume and weight of GAC were 0.5 L and 0.24 kg, respectively.

Subsequently, $H_2S$ gas (10000 ppm) supplied from a gas cylinder was diluted to 3000 ppm $H_2S$ with compressed air and pumped upward through the column at the bottom. The results of the biofilter showed that the bacterium had remarkable removal efficiency of $H_2S$. In other words, the bacterium was an acidophilic sulfide-oxidizing bacterium and able to oxidize $H_2S$ into sulfate, i.e., reducing $H_2S$ concentration. Accordingly, the bacterium was identified as the following.

First, the genomic DNA was extracted and purified by a DNA kit (Geneaid Biotech Ltd.). A primer set specific for bacteria was provided, in which forward primer 9F was GAGTTTGATCCTGGCTCAG (SEQ ID No. 1), and reverse primer 1543R was AGAAAGGAGGTGATCCAGC (SEQ ID No. 2). Using the primer set, 16S rDNA of the bacterium was amplified by polymerase chain reaction (PCR) and analyzed by DNA sequencing. The sequence of 16S rDNA of the bacterium is shown as the following.

[SEQ ID No. 3]
TGCTAGATGCAGTCGAGCGGTGCATGTTTATACCTGTTCA

GCGGCGGACGGGTGAGTAACGCGTGGGTGACCTACCCGGAAG

AGGCGGACAACCTGGGGAAACCCAGGCTAATCCGCCATGTGG

TCCTGTCCTGTGGGGCAGGACTAAAGGGTGGATAGCCCGCTTC

CGGATGGGCCCGCGTCCCATCAGCTAGTTGGTGGGGTAAAGGC

CCACCAAGGCGACGACGGGTAGCCGGTCTGAGAGGATGGCCG

GCCACAGGGGCACTGAGACACGGGCCCCACTCCTACGGGAGG

CAGCAGTTACGAATCTTCCGCAATGGACGGAAGTCTGACGGAG

CGACCCCGCTTGGAGGAGGAAGCCCTTCGGGGTGTAAACTCCT

GAACTGGGGACGAAAGCCCTGTGTAGGGGGATGACGGTACCC

AGGTAATAGCGCCGGCCAACTCCGTGCCAGCAGCCGCGGTAAT

ACGGAGGGCGCGAGCGTTACCCGGATTTACTGGGCGTAAAGG

-continued

```
GCGTGTAGGCGGCCTGGGCGTCCCATGTGAAAGGCCACGGCT

CAACCGTGGAGGAGCGTGGGATACGCTCAGGCTAGAGGGTGG

GAGAGGGTGGTGGAATTCCCGGAGTAGCGGTGAAATGCGCAG

ATACCGGGAGGAACGCCGATGGCGAAGGCAGCCACCTGGTCC

ACTTCTGACGCTGAGGCGCGAAAGCGTGGGGAGCAAACCGGA

TTAGATACCCGGGTAGTCCACGCCCTAAACGATGCGCGCTAGG

TCTTTGGGGTTTATCTGGGGGCCGAAGCCAACGCGTTAAGCGC

GCCGCCTGGGGAGTACGGCCGCAAGGCTGAAACTCAAAGGAA

TTGACGGGGCCCGCACAAGCGGTGGAGCATGTGGTTTAATTC

GAAGCAACGCGAAGAACCTTACCAGGCCTTGACATGCTGGGG

AACCTAGGTGAAAGCCTGGGGTGCCCGCGAGGGAGCCCCAGC

ACAGGTGCTGCATGGCCGTCGTCAGCTCGTGTCGTGAGATGTT

GGGTTAAGTCCCGCAACGAGCGCAACCCCTGCCCTTAGTTGCC

AGCGGGTTGGGCCGGGCACTCTAAGGGGACTGCCTGCGAAAG

CAGGAGGAAGGCGGGACGACGTCTGGTCATCATGGCCCTTAC

GGCCTGGGCGACACACGTGCTACAATGCCCACTACAGAGCGA

GGCGACCCAGTGATGGGGAGCGAATCGCAAAAAGGTGGGCGT

AGTTCGGATTGGGGTCTGCAACCCGACCCCATGAAGCCGGAAT

CGCTAGTAATCGCGGATCAGCCATGCCGCGGTGAATACGTTCC

CGGGCCTTGTACACACCGCCCGTCACGCCATGGGAGCGGGTTC

TACCCGAAGTCGCCGGGAGCCTTAGGGCAGGCGCCGAGGGTA

GGGCTCGTGACT
```

Then, the above sequence was aligned and compared with available standard sequences of bacterial lineage in the National Center for Biotechnology Information (NCBI) Gen-Bank using Basic Local Alignment Search Tool (BLAST). The phylogenetic tree was constructed using the neighbor-joining method (Saitou & Nei, 1987) via the MEGA 3.1 software with 1000 bootstrap replicates.

The results showed that the sulfide-oxidizing bacterium of the present example was classified in *Thermus* sp. In the present invention, the bacterium is named as *Thermus* sp. CP1.

Example 2

Oxidative Activity of Sulfide-Oxidizing Bacterium *Thermus* sp. CP1 to $H_2S$

Removal Efficiency of $H_2S$ for Continuous Operation

First, with reference to FIG. 1, a schematic diagram of a field biofilter used in the present example is shown. In the field biofilter, elimination of $H_2S$ in biogas emitted from an anaerobic swine wastewater treatment system was measured.

As shown in FIG. 1, the biogas emitted from the swine wastewater treatment system 3 was introduced into an air-mixing bottle 8 by an exhaust fan 1. A flow meter 2 was connected therebetween to adjust the amount of biogas. An air compressor was used to compress air and was connected with another exhaust fan 1 and flow meter 2.

In addition, as described in the example mentioned above, the bacterium-immobilized GAC was packed into a column 5 (diameter 12 cm and height 65 cm) of the field biofilter. In the column, the packed volume and weight of GAC were 5 L and 2.4 kg, respectively. The bottom of the column 5 had an outlet 53 connected to a nutrient bottle 4. The culture medium of the nutrient bottle 4 was introduced through the column 5 from an inlet 54 by a peristaltic pump 6 and adjusted to a flow rate of 1 L/min by a regulator 7. The culture medium was supplied for 30 min per day. The air inlet 51 at the bottom of the column 5 was connected to the air-mixing bottle 8. The biogas of the air-mixing bottle 8 was charged from the air inlet 51 upward through the column 5 and discharged from an air outlet 52. During the gas supply, the flow rate of biogas was controlled at 150 L/hr.

The field biofilter was operated for eight hours per day. In order to estimate the operating performance of the biofilter for $H_2S$ removal efficiency, the gas was supplied at the empty bed gas residence times (EBRTs) of 60 and 120 s. The EBRT was defined as the volume of the packed bed divided by the gas flow rate. During the operation of the field biofilter, $H_2S$ gas concentrations at the inlet and the outlet of the column were determined by gas detector tubes (Kitagawa) ranging between 0.05% and 2% (detectable minimum concentration: 100 ppm) and between 0.01% and 0.2% (detectable minimum concentration: 50 ppm).

The $H_2S$ removal rate in the bacterium-immobilized biofilter was calculated using the following equation derived from the following Michaelis-Menten equation (Hirai et al., 1990).

$$1/R = K_s/V_m * 1/C_{ln} + 1/V_m$$

In the equation, R (g m$^{-3}$ h$^{-1}$) is removal rate, $C_{ln}$ (g m$^{-3}$) is the logarithmic mean concentration of $H_2S$ at the inlet and outlet of the biofilter, $V_m$ (g m$^{-3}$ h$^{-1}$) is the maximum removal rate, and $K_s$ (g m$^{-3}$) is the saturation constant.

For bacterial number estimation, 0.5 g GAC was taken out from the sample port and mixed with 5 mL sterile water. The sample was vortexed for 3 min, and the bacterial numbers on the support material of the biofilter system were determined after dilution by the plating count technique. Sulfate concentration in the biofilter was analyzed by a spectrophotometer according to the Sulfate Reagent, SulfaVer® 4 (Hach). The results of the above experiments are shown in FIGS. 2 to 6.

Figure 2:
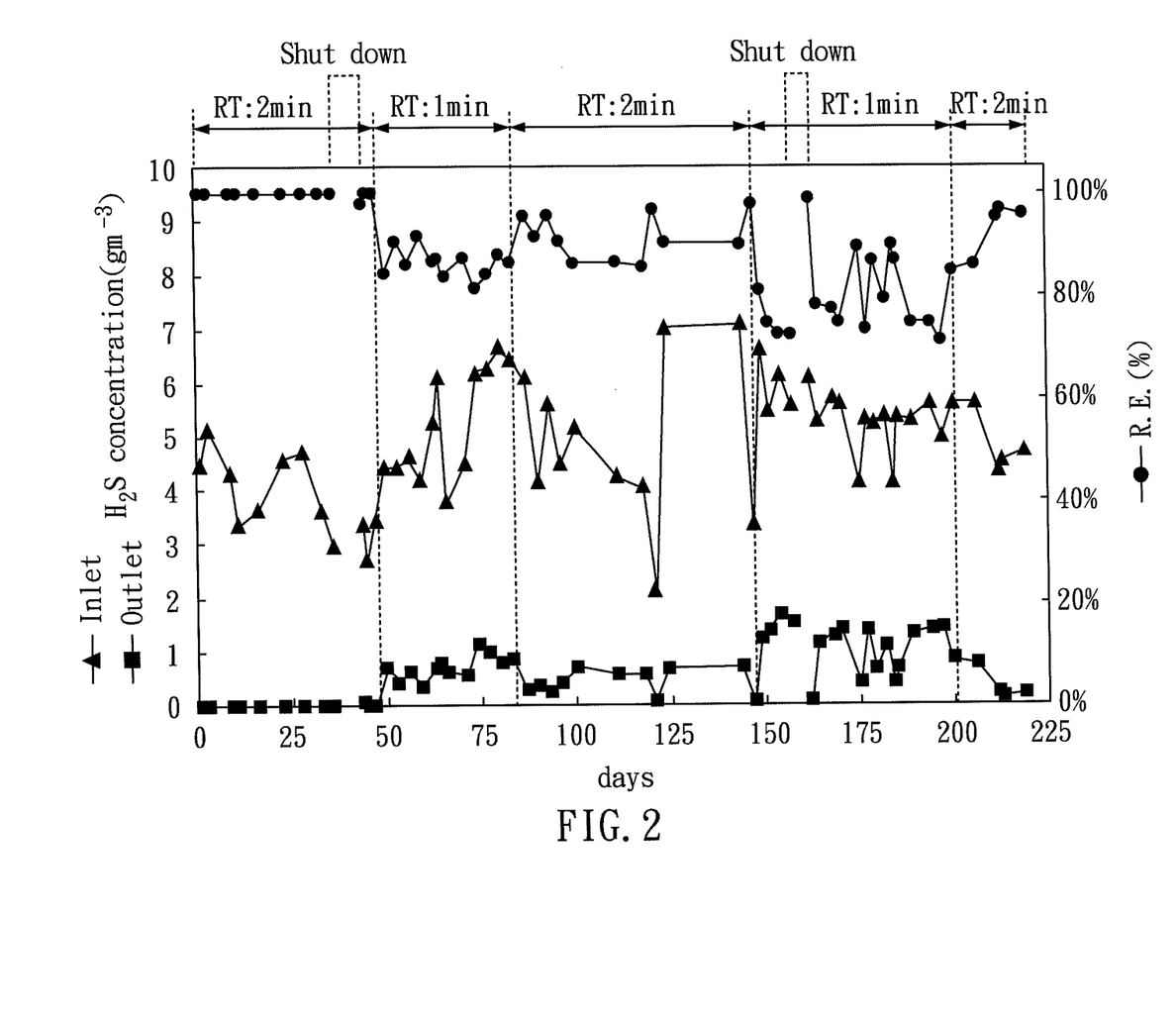
FIG. 2 is a line chart of changes of $H_2S$ concentration and removal efficiency (R.E. (%)) in Example 2 of the present invention, wherein the dot mark denotes removal efficiency of $H_2S$, the triangle mark denotes $H_2S$ concentration at the inlet of the field biofilter, and the square mark denotes $H_2S$ concentration at the outlet of the field biofilter.

FIG. 2 shows the influence of factors such as EBRT, shutdown timing, and $H_2S$ concentration in the biogas to the $H_2S$ removal efficiency during the continuous operation of the field biofilter. In FIG. 2, the dot mark denotes removal efficiency of $H_2S$, the triangle mark denotes $H_2S$ concentration at the inlet of the field biofilter, and the square mark denotes $H_2S$ concentration at the outlet of the field biofilter. Based on FIG. 2, when the flow rate of the biogas is 150 L/hr and the EBRT is 2 minutes, the average $H_2S$ removal efficiency can reach approximately 95%.

Figure 3:
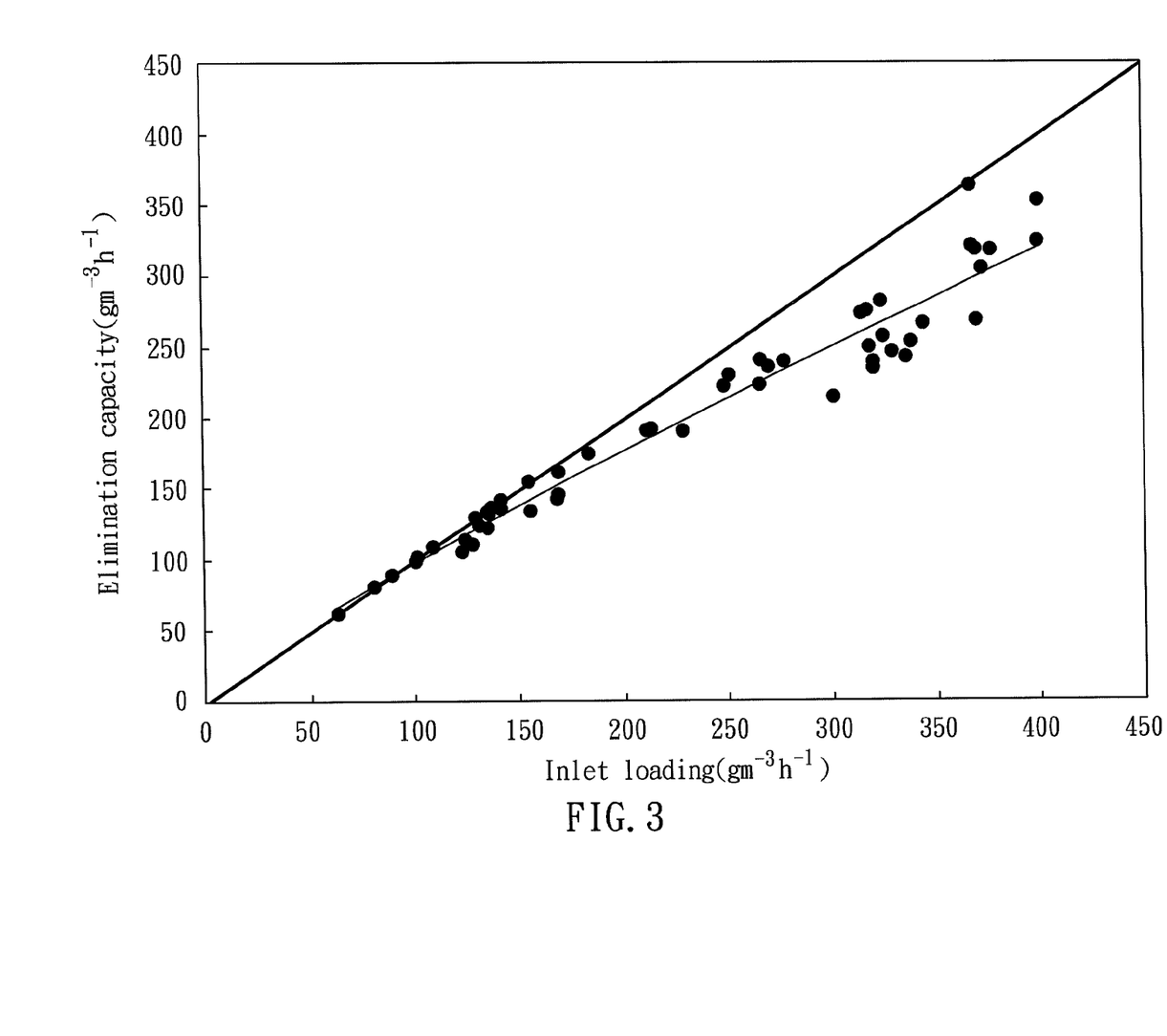
FIG. 3 shows a line chart of the relationship between the inlet loading and the elimination capacity of $H_2S$ in Example 2 of the present invention.
Figure 4:
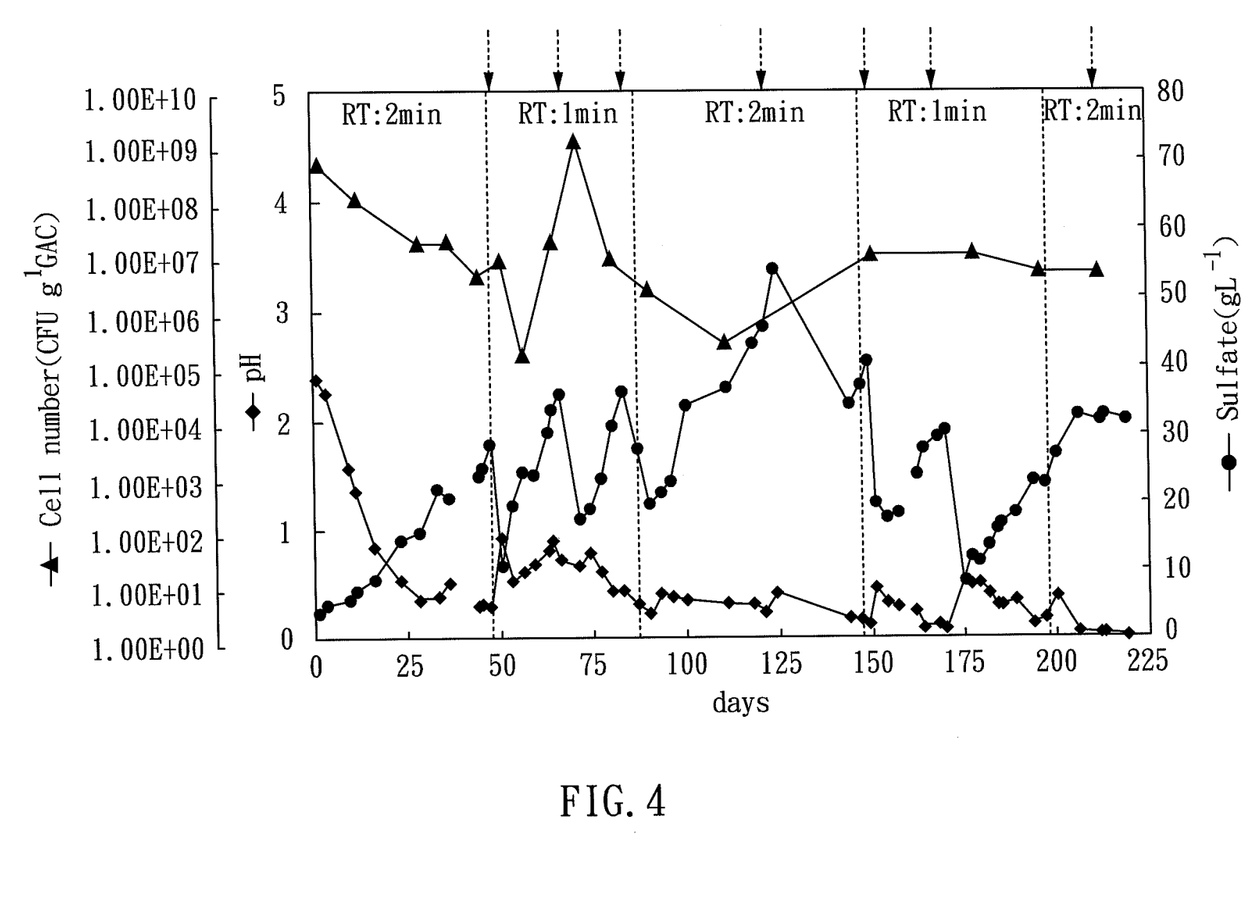
FIG. 4 shows a line chart of changes among pH value, cell number and sulfate concentration in Example 2 of the present invention, wherein the dot mark denotes sulfate concentration, the triangle mark denotes cell number, the rhombus mark denotes pH value, and the arrow mark means the time point of supplying fresh medium.

FIG. 3 shows the relationship between the inlet loading and the elimination capacity of $H_2S$. With reference to FIG. 3, when the inlet loading of $H_2S$ is about 400 g m$^{-3}$ hr$^{-1}$, the maximum $H_2S$ elimination capacity reaches approximately 352 g m$^{-3}$ hr$^{-1}$. Furthermore, FIG. 4 shows the changes among pH value, cell number and sulfate concentration during continuous operation of the field biofilter. In FIG. 4, the dot mark denotes sulfate concentration, the triangle mark denotes cell number, the rhombus mark denotes pH value, and the arrow mark means the time point of supplying fresh medium. Based on FIG. 4, when the pH value is lower than 1 and the sulfate concentration reaches 54 g L$^{-1}$, the number of the acidophilic sulfide-oxidizing bacterium of the present invention immobilized on the support material still reaches 10$^6$-10$^7$ CFU per gram of GAC.

Figure 5:
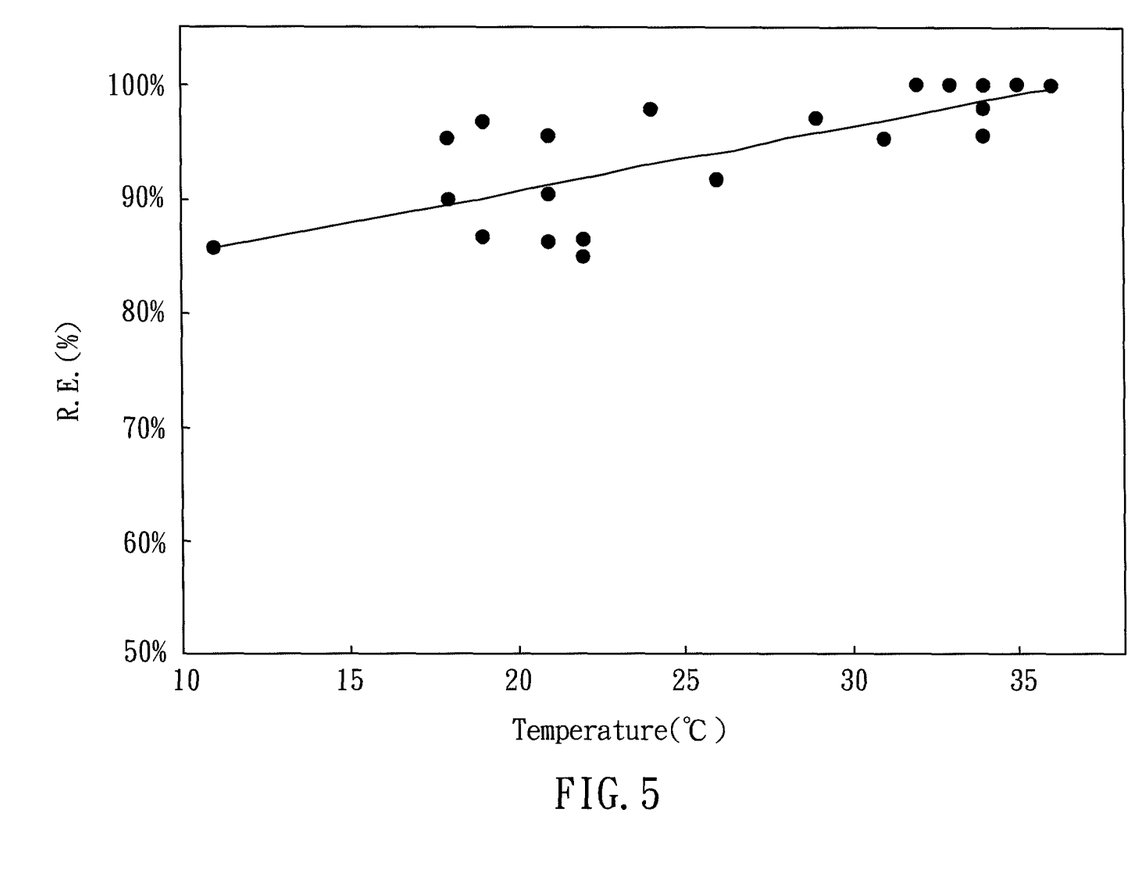
FIG. 5 shows a line chart of the relationship between the temperature and the removal efficiency of $H_2S$ in Example 2 of the present invention, wherein the empty bed gas residence time (EBRT) is 2 minutes.

Moreover, FIG. 5 shows the relationship between the temperature and the removal efficiency of $H_2S$ if the EBRT is 2 minutes. As shown in FIG. 5, when the temperature rises to about 35° C., the acidophilic sulfide-oxidizing bacterium of the present invention is able to achieve 100% $H_2S$ removal efficiency. In addition, after the analysis of the sulfur equilibrium, it was found that 50% of $H_2S$ was transformed into ionic sulfate.

Figure 6:
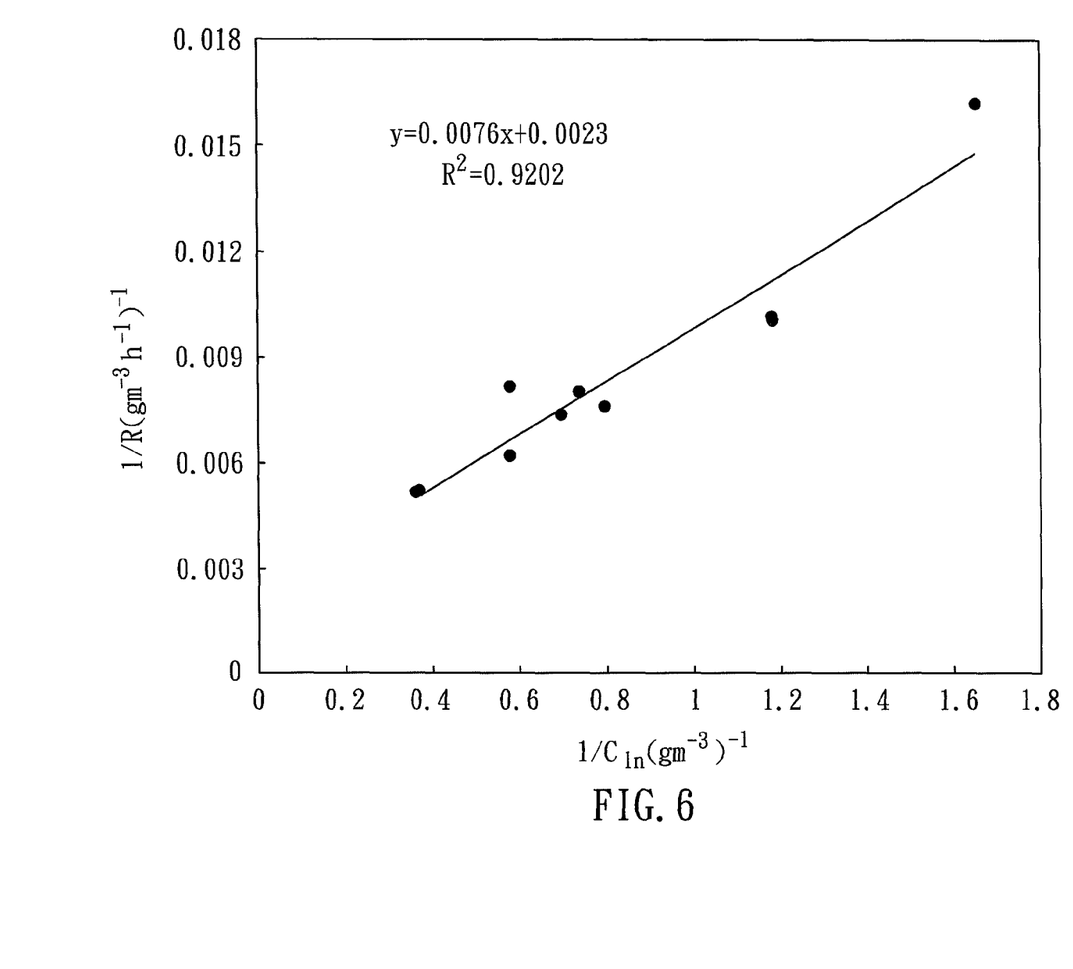
FIG. 6 shows a linear regression chart of $1/R$ vs. $1/C_{In}$ in kinetics analysis in Example 2 of the present invention, wherein the gas flow rate is controlled in 150 L/hr, biogas concentration ranges from 1,500 to 5,000 ppm, and EBRT is 2 minutes.

FIG. 6 shows a linear regression chart of $1/R$ vs. $1/C_{in}$ in kinetics analysis. In FIG. 6, the gas flow rate is controlled in 150 L/hr, biogas concentration ranges from 1,500 to 5,000 ppm, and EBRT is 2 minutes. According to the slope and the intercept of the line shown in FIG. 6, the $V_m$ and $K_s$ values of the immobilized acidophilic sulfide-oxidizing bacterium of the present invention are 434.8 g m$^{-3}$ hr$^{-1}$ and 3.3 g m$^{-3}$, respectively. The $K_s$ value of the acidophilic sulfide-oxidizing bacterium (*Thermus* sp. CP1) of the present invention is significantly lower than the $K_s$ value (5.2 g m$^{-3}$) of a known microbe, *Alcaligenes faecalis*, (Rattanapan et al., 2010). This result demonstrates that the acidophilic sulfide-oxidizing bacterium of the present invention has better affinity to $H_2S$. Besides, when *A. faecalis* is used to process $H_2S$, the main product (i.e., S) precipitates in the reaction. If *A. faecalis* is applied in the system for removing $H_2S$, S precipitate possibly incurs problems such as obstruction and short circuiting of the system. By contrast, the acidophilic sulfide-oxidizing bacterium (*Thermus* sp. CP1) of the present invention transforms $H_2S$ into sulfate and thus the above-mentioned problems can be avoided.

Although the research (Duan, H. Q. et al., 2006) has shown that endobacteria of activated sludge immobilized on activated carbon can be used for $H_2S$ removal, the elimination capacity and the removal efficiency only reaches 181 g m$^{-3}$ h$^{-1}$ and 94%, respectively, and the $H_2S$ concentration (about 87 ppm) of supplied gas is far lower than that of the field biogas. By contrast, in the experiments mentioned above, the acidophilic sulfide-oxidizing bacterium (*Thermus* sp. CP1) of the present invention can remove the high $H_2S$ concentration of the field biogas. When the inlet loading of $H_2S$ is 400 g m$^{-3}$ hr$^{-1}$, the composite of the present invention can achieve the maximum for $H_2S$ removal, about 352 g m$^{-3}$ hr$^{-1}$, far higher than that of the conventional research.

Example 3

$H_2S$ Removal Efficiency of Known *Thermus* sp

Figure 7:
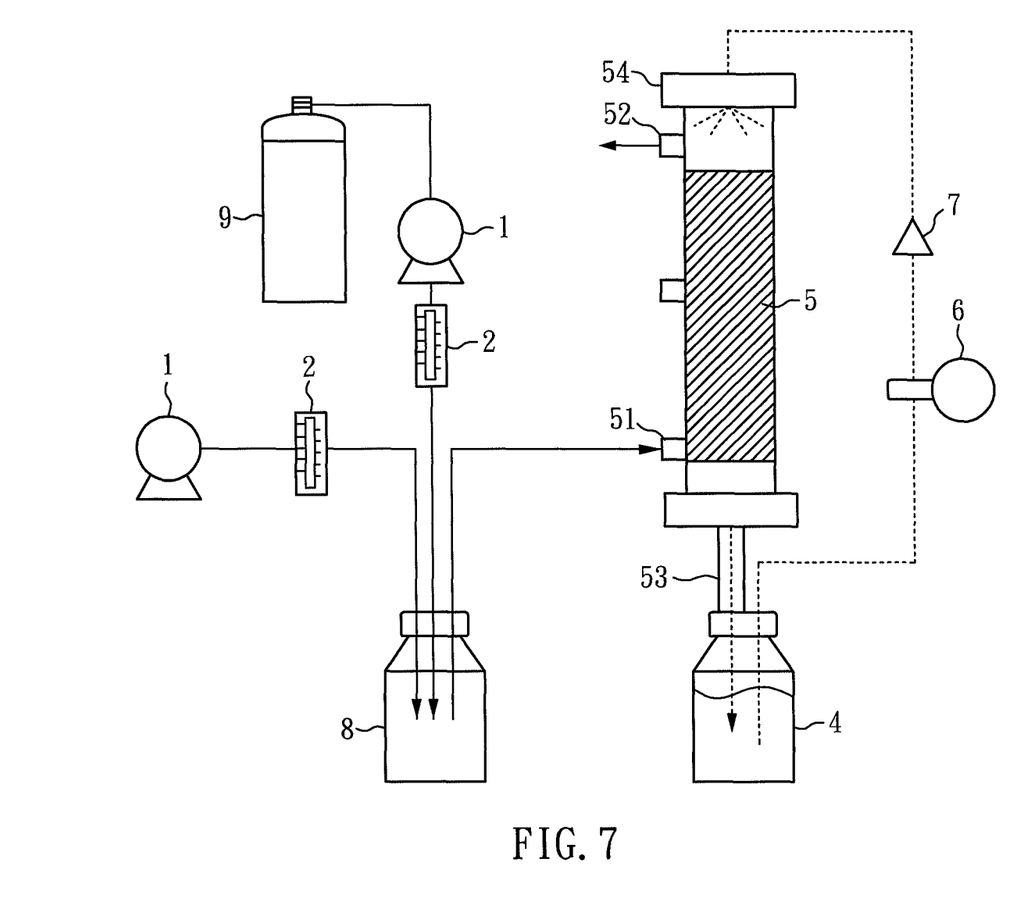
FIG. 7 is a schematic diagram of a lab-scaled field biofilter employed in Example 3 of the present invention.

As the method described in Example 1, *Thermus scotoductus* (ATCC 51532, purchased from BCRC in Hsinchu, Taiwan) was immobilized on GAU and packed into a column 5 (diameter 5.4 cm and height 35 cm) of the field biofilter as shown in FIG. 7. In the column, the packed volume of GAC was 500 mL. $H_2S$ gas (10000 ppm) supplied from a gas cylinder 9 pumped into an air-mixing bottle 8 by an exhaust fan 1. A flow meter 2 was connected therebetween to adjust the amount of $H_2S$. An air compressor was used to compress air and connected with another exhaust fan 1 and flow meter 2.

The air was supplied into the air-mixing bottle 8 to dilute $H_2S$ to 5.6 g/m$^3$ (4,000 ppm). The gas mixture was charged from an air inlet 51 at the bottom of the column 5 upward through the column 5 and then discharged from an air outlet 52 at the top of the column 5. During the reaction, an outlet 53 at the bottom of the column 5 was connected to a nutrient bottle 4. The culture medium of the nutrient bottle 4 was introduced through the column 5 from an inlet 54 by a peristaltic pump 6 and adjusted in a stable flow rate by a regulator 7. After long-term operation of 28 days, $H_2S$ gas concentrations were determined by gas detector tubes (Kitagawa) with different detectable concentration ranges during the operation of the field biofilter. The result is shown in FIG. 8.

Figure 8:
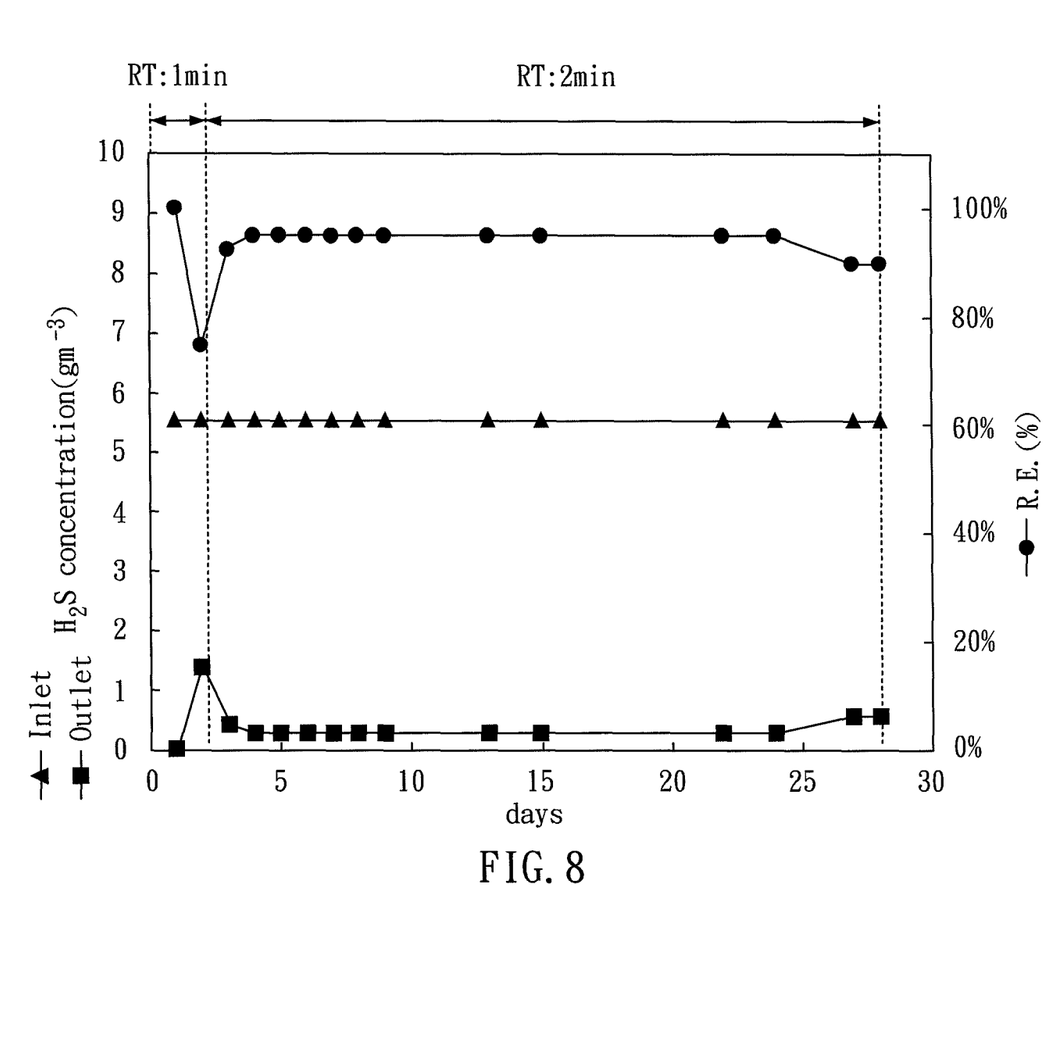
FIG. 8 shows a line chart of changes of $H_2S$ concentration and removal efficiency in Example 3 of the present invention, wherein the dot mark denotes removal efficiency of $H_2S$, the triangle mark denotes $H_2S$ concentration at the inlet of the field biofilter, and the square mark denotes $H_2S$ concentration at the outlet of the field biofilter.

FIG. 8 shows the changes of $H_2S$ concentration and removal efficiency. In FIG. 8, the dot mark denotes removal efficiency of $H_2S$, the triangle mark denotes $H_2S$ concentration at the inlet of the field biofilter, and the square mark denotes $H_2S$ concentration at the outlet of the field biofilter. According to FIG. 8, it can be seen that *Thermus scotoductus* is able to maintain $H_2S$ removal efficiency about 90% or more when the gas retention time is 2 minutes. In the condition of flow loading 167 g m$^{-3}$ h$^{-1}$, the maximum loading removal rate is 159 g m$^{-3}$ h$^{-1}$. This result indicates that *Thermus scotoductus* has good performance for $H_2S$-removal.

In conclusion, the biological composite and the method for reducing $H_2S$ and the acidophilic sulfide-oxidizing bacterium of the present invention can stably reduce $H_2S$ in processes such as petrochemical oil-refining, production of biogas and natural gas, and papermaking (i.e., $H_2SO_4$ is easily accumulated with the proceeding processes). Even if $H_2SO_4$ is accumulated along with the increase in reaction time to reduce the environmental pH value, the biological composite and the method for reducing $H_2S$ and the acidophilic sulfide-oxidizing bacterium of the present invention are still able to maintain $H_2S$ removal efficiency. Therefore, $H_2S$ erosion to machines or lethal effects on humans can be avoided.

Although the present invention has been explained in relation to its preferred embodiment, it is to be understood that many other possible modifications and variations can be made without departing from the spirit and scope of the invention as hereinafter claimed.

What is claimed is:

1. A biological method for decreasing the amount of H₂S in a gas sample, comprising the following steps:
    making a biologically pure culture of *Thermus* sp. bacterium in contact with the gas sample; and
    oxidizing the H₂S with the bacteria thereby decreasing the amount of H₂S,
    wherein the 16S rDNA sequence of the *Thermus* sp. bacterium is SEQ ID NO. 3.

2. The method of claim 1, wherein the *Thermus* sp. bacterium is immobilized on a carrier.

3. The method of claim 2, wherein the carrier is at least one selected from a group consisting of activated carbon, peat soil, compost, bark, vermiculite, oyster shell, zeolite, porphyritic andesite, iron hydroxide, active alumina, pearlite, snakewood, and artificially synthesized chemical materials.

4. The method of claim 3, wherein the *Thermus* sp. bacterium forms a biofilm encompassing the carrier.

5. The method of claim 1, wherein the *Thermus* sp. bacterium is deposited BCRC 910527 in Bioresource Collection and Research Center in Hsinchu, Taiwan.

\* \* \* \* \*

SEQUENCE LISTING

<160> NUMBER OF SEQ ID NOS: 3

<210> SEQ ID NO 1
<211> LENGTH: 19
<212> TYPE: DNA
<213> ORGANISM: Artificial
<220> FEATURE:
<223> OTHER INFORMATION: Forward primer

<400> SEQUENCE: 1
gagtttgatc ctggctcag                                              19

<210> SEQ ID NO 2
<211> LENGTH: 19
<212> TYPE: DNA
<213> ORGANISM: Artificial

-continued

```
<220> FEATURE:
<223> OTHER INFORMATION: Reverse primer

<400> SEQUENCE: 2
agaaaggagg tgatccagc                                                    19

<210> SEQ ID NO 3
<211> LENGTH: 1411
<212> TYPE: DNA
<213> ORGANISM: Thermus sp.

<400> SEQUENCE: 3
tgctagatgc agtcgagcgg tgcatgttta tacctgttca gcggcggacg ggtgagtaac      60
gcgtgggtga cctacccgga agaggcggac aacctgggga aacccaggct aatccgccat     120
gtggtcctgt cctgtgggc aggactaaag ggtggatagc ccgcttccgg atgggcccgc      180
gtcccatcag ctagttggtg gggtaaaggc ccaccaaggc gacgacgggt agccggtctg     240
agaggatggc cggccacagg ggcactgaga cacgggcccc actcctacgg gaggcagcag    300
ttacgaatct tccgcaatgg acggaagtct gacggagcga ccccgcttgg aggaggaagc    360
ccttcggggt gtaaactcct gaactgggga cgaaagccct gtgtaggggg atgacggtac   420
ccaggtaata gcgccggcca actccgtgcc agcagccgcg gtaatacgga gggcgcgagc    480
gttacccgga tttactgggc gtaaaggggcg tgtaggcggc ctggggcgtc ccatgtgaaa  540
ggccacggct caaccgtgga ggagcgtggg atacgctcag gctagagggt gggagagggt    600
ggtggaattc ccggagtagc ggtgaaatgc gcagataccg ggaggaacgc cgatggcgaa    660
ggcagccacc tggtccactt ctgacgctga ggcgcgaaag cgtggggagc aaaccggatt   720 agataccccgg gtagtccacg ccctaaacga tgcgcgctag gtctttgggg tttatctggg  780
ggccgaagcc aacgcgttaa gcgcgccgcc tggggagtac ggccgcaagg ctgaaactca    840
aaggaattga cggggccccg cacaagcggt ggagcatgtg gtttaattcg aagcaacgcg   900 aagaaccttta ccaggccttg acatgctggg gaacctaggt gaaagcctgg ggtgcccgcg  960
agggagcccc agcacaggtg ctgcatggcc gtcgtcagct cgtgtcgtga gatgttgggt   1020
taagtcccgc aacgagcgca accctgccc ttagttgcca gcgggttggg ccgggcactc  1080 taagggggact gcctgcgaaa gcaggaggaa ggcggggacg acgtctggtc atcatggccc 1140
ttacggcctg ggcgacacac gtgctacaat gcccactaca gagcgaggcg acccagtgat 1200
ggggagcgaa tcgcaaaaag gtgggcgtag ttcggattgg ggtctgcaac ccgaccccat 1260
gaagccggaa tcgctagtaa tcgcggatca gccatgccgc ggtgaatacg ttcccggcc   1320 ttgtacacac cgcccgtcac gccatgggag cgggttctac ccgaagtcgc cgggagcctt 1380
agggcaggcg ccgagggtag ggctcgtgac t                                  1411
```